(12) United States Patent
Torres-Ortiz

(10) Patent No.: US 8,707,970 B2
(45) Date of Patent: Apr. 29, 2014

(54) PORTABLE ORAL HYGIENE SYSTEM

(76) Inventor: Migdalia Torres-Ortiz, Coamo, PR (US)

( * ) Notice: Subject to any disclaimer, the term of this patent is extended or adjusted under 35 U.S.C. 154(b) by 148 days.

(21) Appl. No.: 13/396,284

(22) Filed: Feb. 14, 2012

(65) Prior Publication Data

US 2013/0206162 A1 Aug. 15, 2013

(51) Int. Cl.
*A45D 44/18* (2006.01)
*A46B 15/00* (2006.01)
*A46B 11/00* (2006.01)

(52) U.S. Cl.
USPC .......................................... 132/309; 132/311

(58) Field of Classification Search
USPC ................... 132/308–311; 15/22.1, 185, 184; 401/155, 191
See application file for complete search history.

(56) References Cited

U.S. PATENT DOCUMENTS

| | | | | |
|---|---|---|---|---|
| 1,659,628 | A * | 2/1928 | Greenblatt | 401/155 |
| 2,399,660 | A * | 5/1946 | Boulicault | 132/311 |
| 2,476,686 | A * | 7/1949 | Smith et al. | 401/191 |
| 4,957,125 | A * | 9/1990 | Yaneza | 132/309 |
| 5,189,751 | A * | 3/1993 | Giuliani et al. | 15/22.1 |
| 5,348,028 | A * | 9/1994 | Gustavel | 132/309 |
| 2002/0121283 | A1* | 9/2002 | Piccolo et al. | 132/309 |
| 2006/0005330 | A1* | 1/2006 | Rehkemper | 15/22.1 |

* cited by examiner

*Primary Examiner* — Robyn Doan
(74) *Attorney, Agent, or Firm* — Ferraiuoli LLC; Eugenio J. Torres-Oyola; Rafael Rodriguez-Muriel

(57) ABSTRACT

An integrated oral health hygiene system including at least one oral health care product such as an electric toothbrush, dental floss and dental rinse/wash. In addition, the system includes a retractable toothbrush and an aperture to storage multiple devices including but not limit to batteries, pills, toothpick and others.

8 Claims, 12 Drawing Sheets

Fig. 25

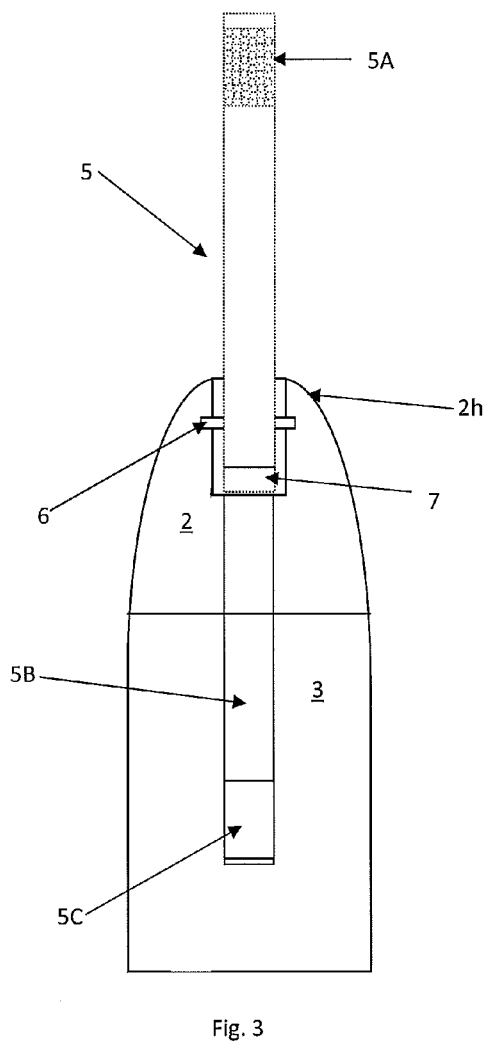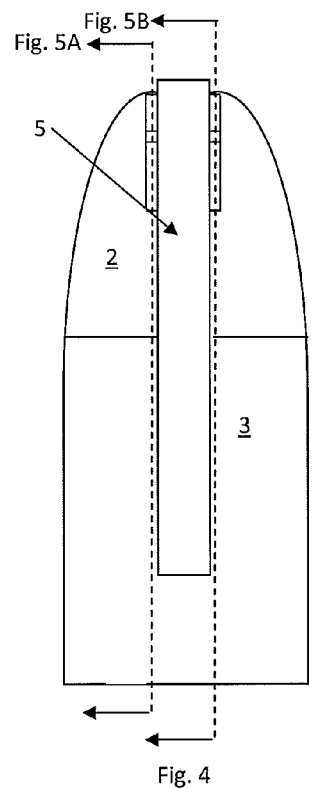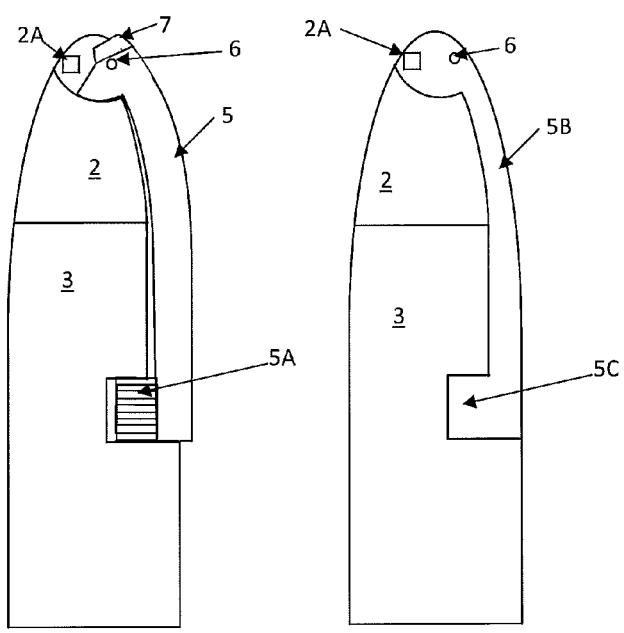
Fig. 3
Fig. 4
Fig. 5A
Fig. 5B

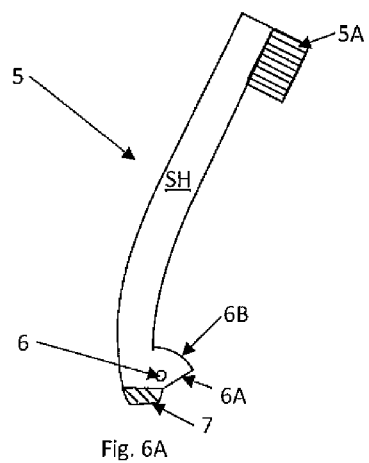
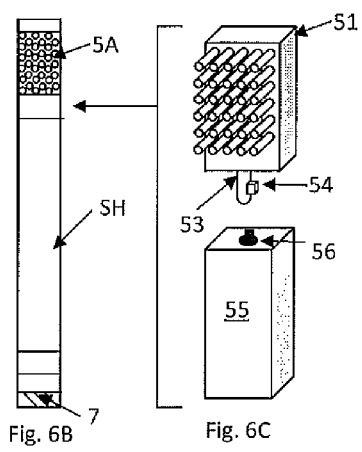
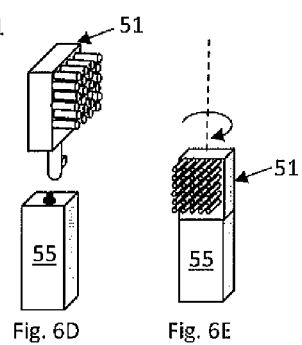
Fig. 6A    Fig. 6B    Fig. 6C    Fig. 6D    Fig. 6E
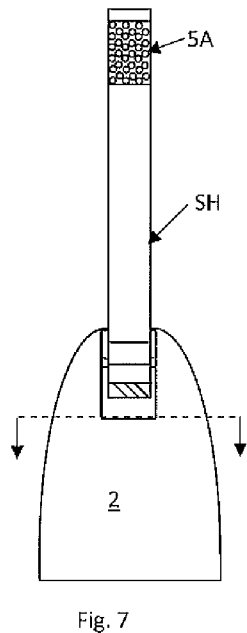
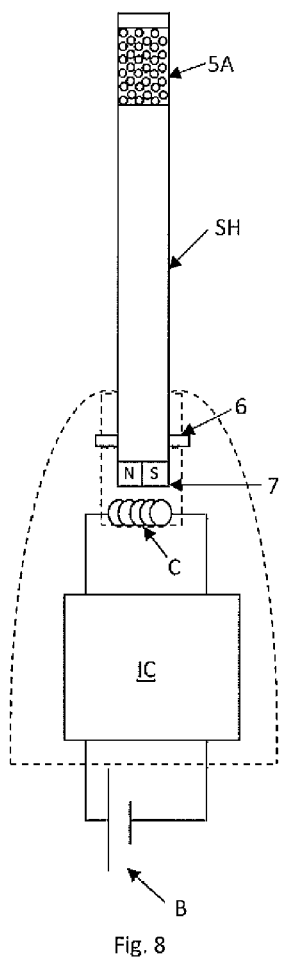
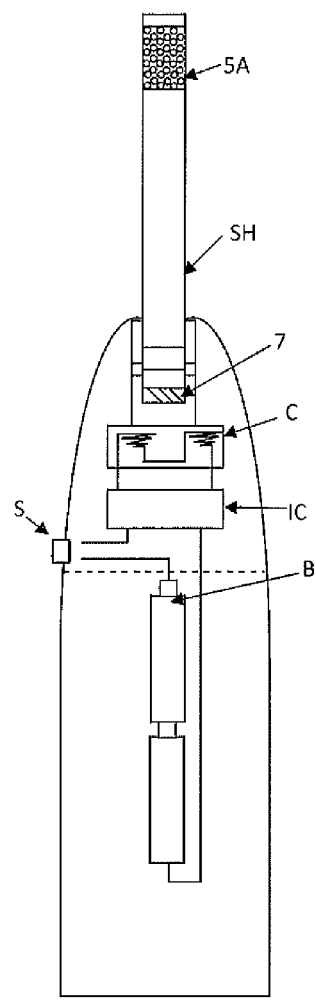
Fig. 7    Fig. 8    Fig. 9

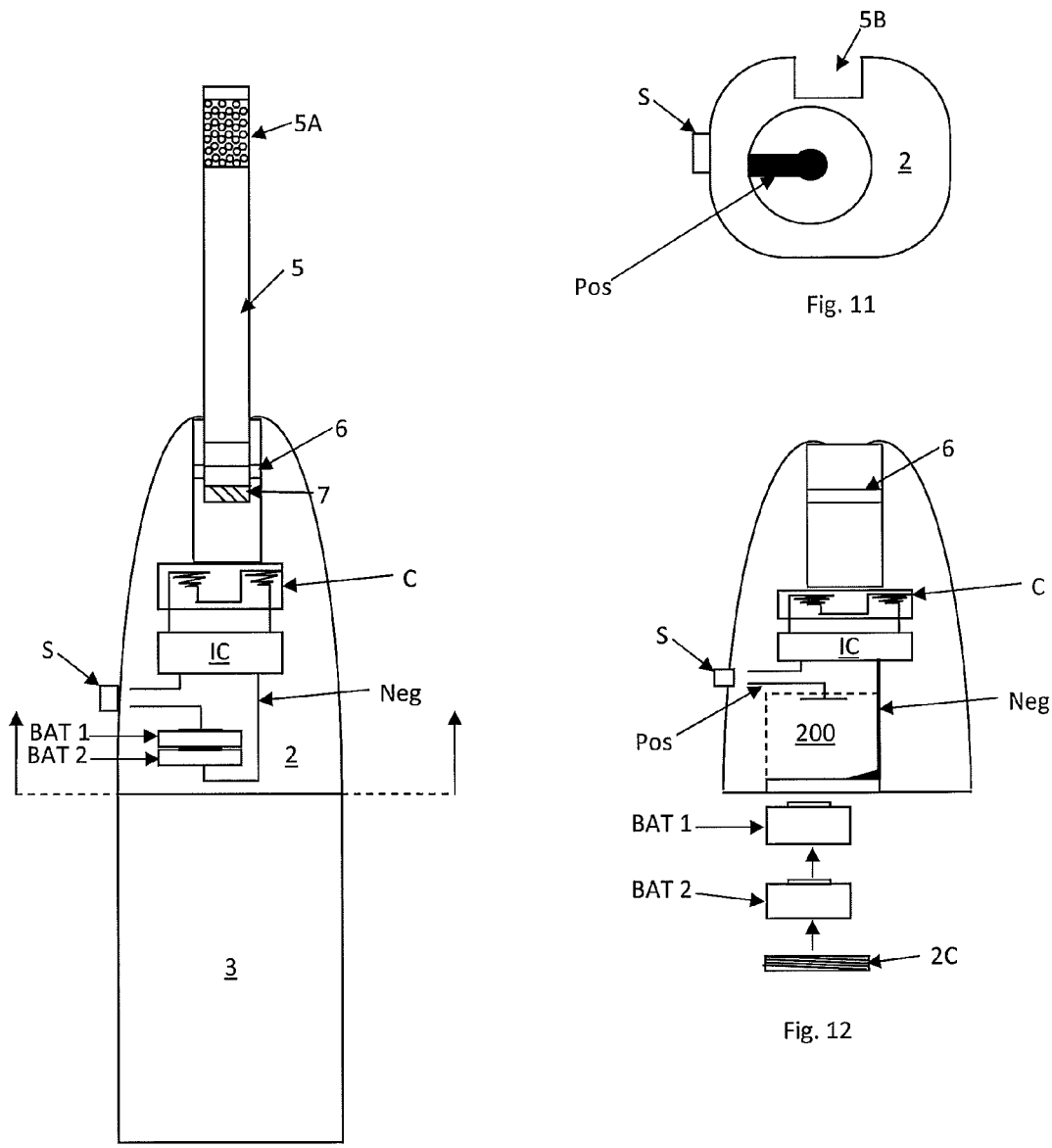
Fig. 10
Fig. 11
Fig. 12
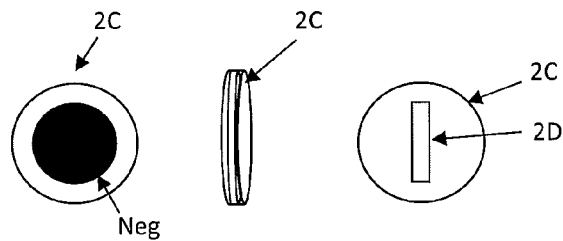
Fig. 13

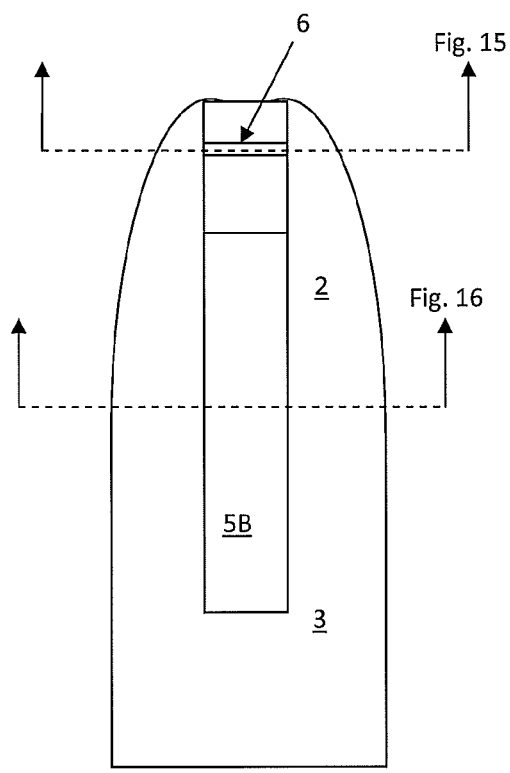
Fig. 14
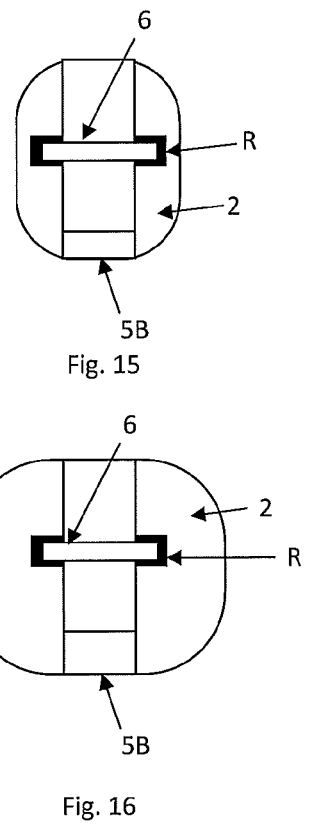
Fig. 15
Fig. 16

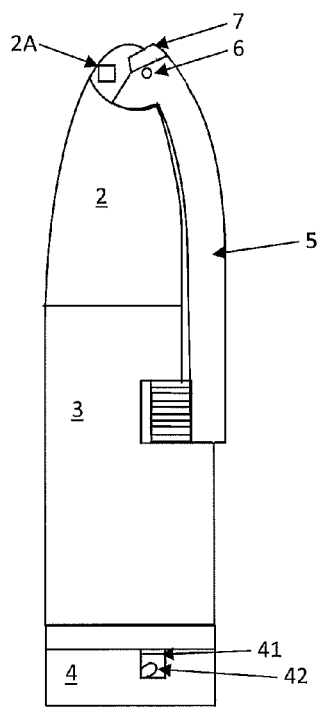
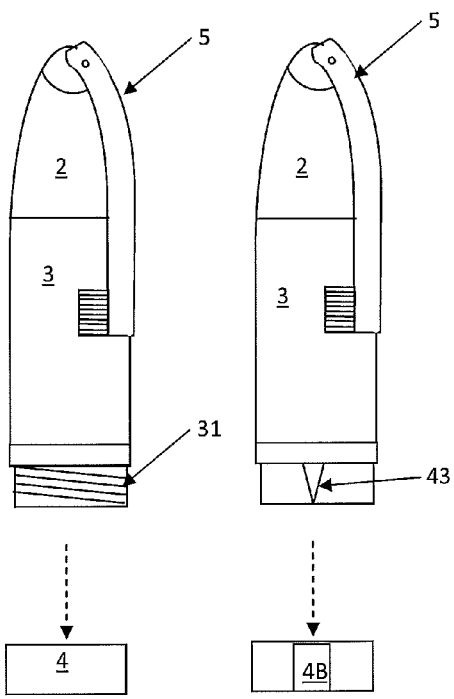
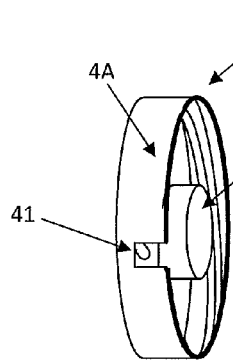
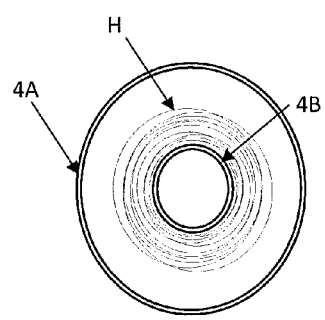
Fig. 17   Fig. 18   Fig. 19   Fig. 20   Fig. 21

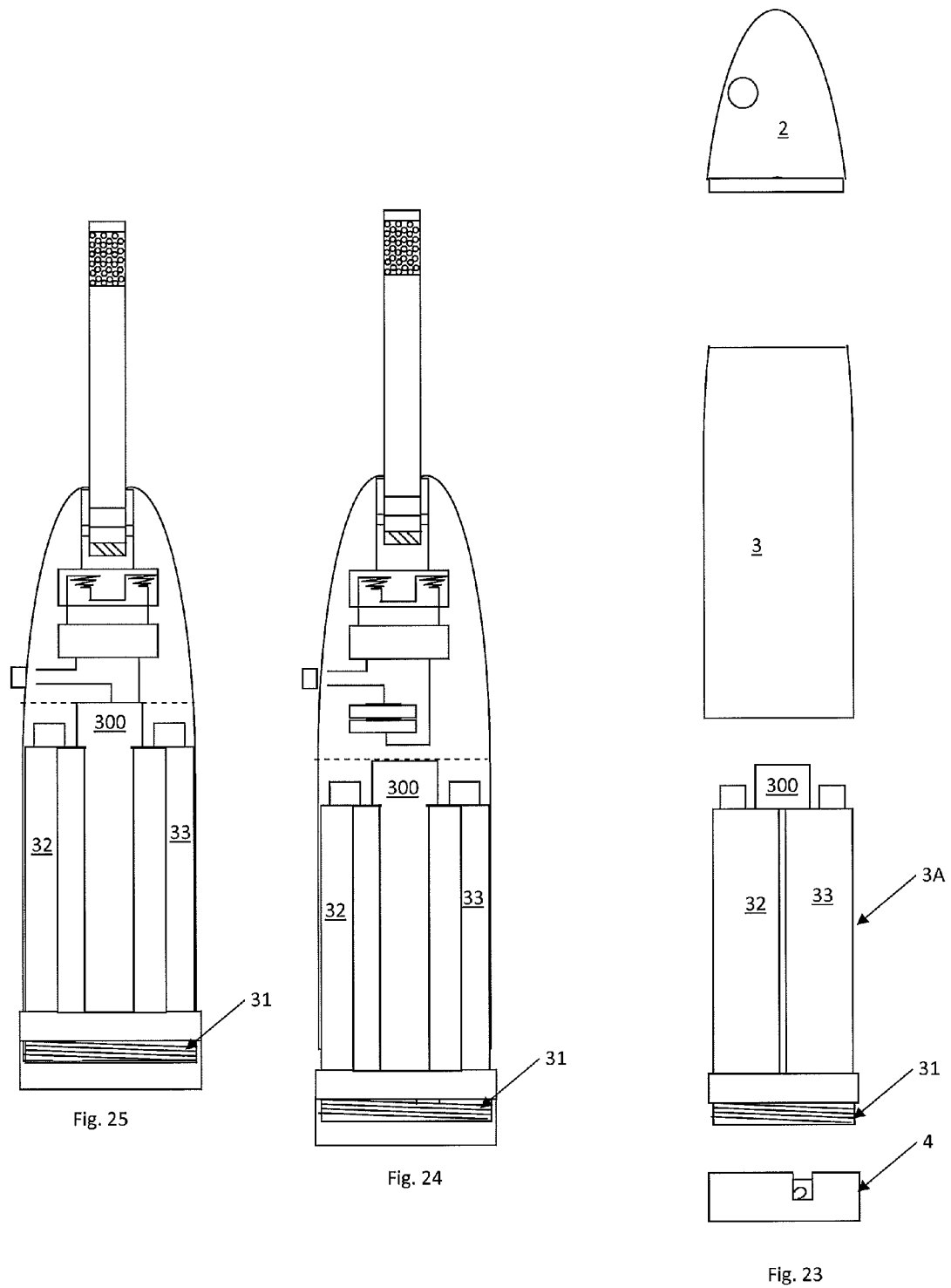

PORTABLE ORAL HYGIENE SYSTEM

STATEMENT REGARDING FEDERALLY SPONSORED RESEARCH AND DEVELOPMENT

N/A

RELATED APPLICATIONS

N/A

BACKGROUND OF THE INVENTION

1. Field of the Invention

The present invention relates to a portable oral hygiene kit, more particularly to a fully, integrated oral health maintenance regimen.

2. Discussion of the Background

Brushing one's teeth is one of the most important parts of healthy hygiene. Good oral hygiene includes regular tooth brushing, flossing, and use of mouthwash in addition to regular visits to a dentist for professional cleaning and general oral care. Good oral hygiene mitigates dental plaque and tartar build-up which can cause, among other things, cavities, gingivitis, premature tooth decay and/or gum disease.

Most of the time people away from home are unable to brush their teeth after lunch or immediately following a snack. The longer food particles remain in the mouth, the more susceptible teeth become to the formation of cavities and decay.

Currently, several devices for tooth brushing, flossing, and mouthwash are provided separately. Having different and separate devices to accomplish oral hygiene increases the space for storing and cost. Further, traveling with the proper products can be a hazard or a problem due to legal requirements and dimensions of the devices used to clean the mouth.

Therefore, there is a need to provide consumers with a compact, convenient and hygienic means of brushing, flossing, and freshening breath while on the go. A compact and portable oral hygiene kit would allow users to have access to proper oral hygiene at all times.

SUMMARY OF THE INVENTION

The present invention overcomes the limitations of the previous toothbrush kits. Accordingly, it is an object of the present invention to provide consumers with a convenient and hygienic means of brushing, flossing, and freshening breath while on the go.

It is another object of the present invention to provide consumers with an effective and expedient means of brushing teeth. This is a practical approach to healthy, oral hygiene and it provides a quick and sanitary solution.

It is therefore an object of this invention to provide an oral hygiene kit with a properly ventilated case that can be carried.

Still another object of the present invention is to provide a compact and portable electric toothbrush assembly with toothpaste, dental floss and with mini breath freshener.

Yet another object of the present invention is to provide a disposable toothbrush assembly with an appurtenance to protect the toothbrush's body from airborne germs and bacteria when not in use.

It is still another object of the invention is to provide a disposable toothbrush assembly integral with an aperture to storage multiple devices including but not limited to batteries, pills and toothpick.

An additional object of the present invention is to provide a portable toothbrush assembly with various toothpastes, dental floss and mouthwash breath freshener that may be economically manufactured.

Another object of the invention is to provide a portable electric toothbrush assembly with retractable toothbrush providing a compact structure.

The invention itself, both as to its configuration and its mode of operation will be best understood, and additional objects and advantages thereof will become apparent, by the following detailed description of a preferred embodiment taken in conjunction with the accompanying drawings.

The Applicant hereby asserts, that the disclosure of the present application may include more than one invention, and, in the event that there is more than one invention, that these inventions may be patentable and non-obvious one with respect to the other.

Further, the purpose of the accompanying abstract is to enable the U.S. Patent and Trademark Office and the public generally, and especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE DRAWINGS

The accompanying drawings, which are incorporated herein, constitute part of the specifications and illustrate the preferred embodiment of the invention.

FIG. 3 shows the retractable section of the portable electric toothbrush in accordance with the principles of the present invention.

FIG. 4 shows the portable electric toothbrush with the brush part retracted in accordance with the principles of the present invention.

FIG. 5A and FIG. 5B show sectional views from FIG. 4 in accordance with the principles of the present invention.

FIG. 6A through FIG. 6E shows the brush part in accordance with the principles of the present invention.

FIG. 7 shows the brush part adjusted to the upper body part of the electric toothbrush in accordance with the principles of the present invention.

FIG. 8 shows the brush part adjusted to the upper body part of the electric toothbrush in combination electric motor in accordance with the principles of the present invention.

FIG. 9 shows the brush part adjusted to the upper body and middle part of the electric toothbrush in combination electric motor in accordance with the principles of the present invention.

FIG. 10 shows the brush part adjusted to the upper body part of the electric toothbrush in combination electric motor and flat batteries in accordance with the principles of the present invention.

FIG. 11 through FIG. 13 show the upper body part battery chamber of the electric toothbrush in combination electric motor and flat batteries in accordance with the principles of the present invention.

FIG. 14 shows a more detailed retractable section of the portable electric toothbrush in accordance with the principles of the present invention.

FIG. 15 and FIG. 16 show sectional views from FIG. 4 in accordance with the principles of the present invention.

FIG. 17 shows a more detailed portable electric toothbrush in accordance with the principles of the present invention.

FIG. 18 and FIG. 19 show the assembling of the lower part or end cap in accordance with the principles of the present invention.

FIG. 20 and FIG. 21 show a more detailed lower part or end cap in accordance with the principles of the present invention.

FIG. 23 shows a more detailed assembling of the portable electric toothbrush in accordance with the principles of the present invention.

FIG. 24 and FIG. 25 show the inner assembling of the portable electric toothbrush with battery chamber in accordance with the principles of the present invention.

DESCRIPTION OF THE PREFERRED EMBODIMENT

Figure 1:
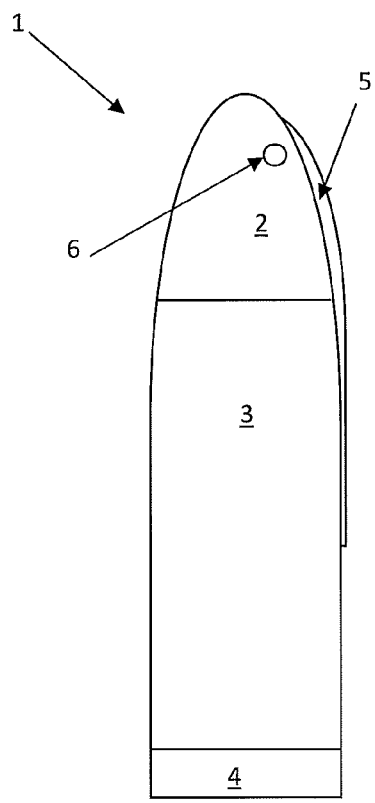
FIG. 1 and FIG. 2 shows the general structure of the present invention in accordance with the principles of the present invention.
Figure 2:
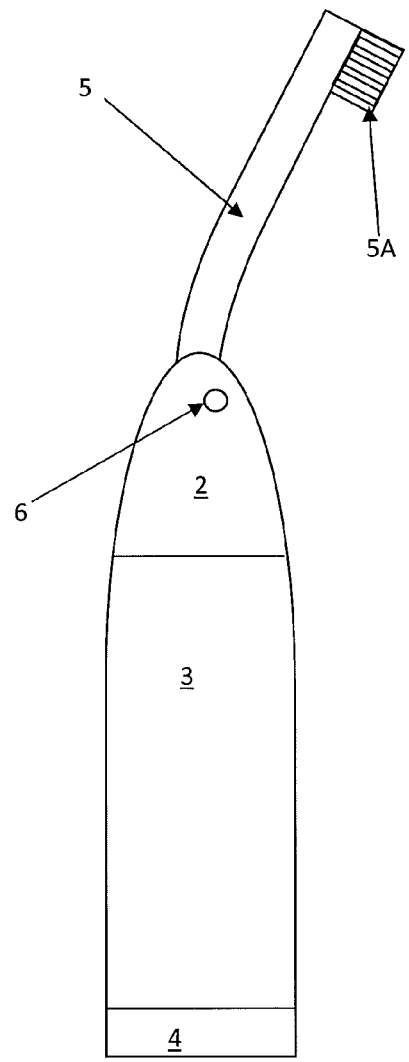

FIG. 1 and FIG. 2 show a portable hygiene kit 1 comprising an electric toothbrush assembly 2 a retractable brush unit 5, a storage section 3 and a flossing unit 4. The retractable brush unit 5 is attached to the electric toothbrush assembly 2 by mean of a pin bar 6 serving as a pivot for the retractable brush 5. The portable hygiene kit 1 is explained in more detail below.

The retractable brush unit is explained in more detail from FIG. 3 to FIG. 6E. The brush unit 5, as shown in FIG. 3, is attached to the electric toothbrush assembling 2 housing 2h by means of a pin bar 6. The brush unit 5 comprises a brush 5A at a first distal end of the brush unit 5 and an interactive zone 7 at a second distal end. A recess 5B, configured to at least receive the brush unit body and brush 5A, extends from the electric toothbrush assembly 2 towards the storage section 3. A first exemplary embodiment in accordance with the principles of the present invention comprises a recess 5B with increasing depth towards the storage unit 3, further the recess 5B have a second recess 5C within, wherein said second recess 5C is configured to fit the brush 5A. FIG. 4 shows the electric toothbrush assembly 2 wherein the retractable brush unit 5 is placed inside the recess 5B. As shown the recess 5B, more particularly a second recess 5C serves as a cover for the brush 5A in order to avoid contact with the environmental hazards and contamination.

FIG. 5A and FIG. 5B shows sectionals from FIG. 4 in accordance with the principles of the present invention. FIG. 5A shows the retractable brush unit 5 inside the recess 5B and second recess 5C. FIG. 5B is directed to the electric toothbrush assembly 2 and storage unit 3 configurations in accordance with the principles of the present invention to fit the brush unit 5. As mentioned the second recess 5C serves as a cover to the brush 5A. Further electric toothbrush assembly 2 comprises a displacement limiter 2A, wherein said displacement limiter 2A limits the retractable brush unit's 5 displacement until reaching a position wherein the interactive zone 7 is efficiently positioned to interact with the actuator, which will be explained below. Further, the retractable brush's position assists for a better reaching of the tooth while holding the portable hygiene kit 1 during mouth washing process.

FIG. 6A through FIG. 6E is directed to the brush unit's 5 details. As mentioned, the brush unit 5 comprises a angled main body or shaft SH with a brush 5A located at a first distal end and an interactive zone 7 at a second distal end in accordance with the principles of the present invention. The interactive zone 7 is selected from a material that interacts with the actuator to provide motion to the brush unit 5. In the instant case the interactive zone 7 is a zone made of magnets which interact with a magnetic field provided by the actuator which is describe below. The brush unit 5 further comprises a sliding section comprising a first curved body 6B and a stop region 6A. The sliding section, more particularly the first curved body 6B slide through an electric toothbrush assembly 2 while being hold with respect to the electric toothbrush assembly's 2 housing 2h by means of pin bar 6. The first curved body 6B comprises a smooth surface which slides over the housing 2h during the retracting and opening process of the retractable brush unit 5.

Further, in the exemplary embodiment of the brush tip in accordance with the principles of the present invention as shown FIG. 6C through FIG. 6E comprises a detachable or changeable brush tip 51, connected to the shaft SH by means of a receiving shaft end 55. The brush tip 51 comprises a locking mean, wherein said locking mean includes a protrusion 53 with a perpendicular extension 54. Receiving shaft end 55 comprises a fixing mean including a recess 56 configured to receive the protrusion 53 with said perpendicular extension 54 for fixing the brush tip 51 to the shaft SH. During the engaging or disengaging process of the removable brush tip 51 the protrusion 53 is aligned with said perpendicular extension 54 to enter the recess 56, as shown in FIG. 6D. Once the protrusion is inserted inside the recess 56, the brush tip 51 is twisted, as shown in FIG. 6E, for fixing the brush tip 51 to the receiving shaft end 55. Recess 56 is shaped to avoid the up and down displacement of the brush tip 51.

FIG. 7 through FIG. 9 are directed to the actuator in accordance with the principles of the present invention. The actuator which is at least partially or completely located inside the electric toothbrush assembly's 2 housing 2h comprises a battery B, integrated circuit IC and a bobbin C. The battery is electrically connected to the coil C in order to supply energy through the integrated circuit IC which controls the current supplied from the battery to the coil C producing a magnetic field. FIG. 8 shows the connection between elements. As presented, the coil C interacts with the interactive zone 7 in order to produce vibration. The IC changes controls the magnetic field polarity at the coil C in such a way that attracts and repulses the interactive zone 7. The coils can be embedded in the following material; ferromagnetic material in order to increase the magnetic field, plastic material with high magnetic permeability in order to avoid damages to the coils or a combination of the both. FIG. 9 is directed to the actuator comprising a switch S to control the activation of the actuator or the flow of energy trough the components.

FIG. 10 through 13 disclose more detail directed to the arrangement of the power supply inside the electric toothbrush assembly 2 housing 2h. A chamber 200 is located inside the electric toothbrush assembling 2 housing 2h providing enough space to fit the power supply or batteries. This first exemplary embodiment in accordance with the principles of the present invention comprises the use of flat batteries BAT1, BAT2 in such way that the space is reduced. A positive terminal POS extending from the chamber 200 is connected to the switch and a negative terminal NEG is connected to integrated circuit IC as show in FIG. 12. Further an opening having a cap 2C provided for the chamber 200 in order to introduce the batteries BAT1, BAT2. The batteries are sealed or water tight inside the chamber 200. The cap 2C comprises a contacting area NEG1 for better contact with the batteries. Further a cap recess 2D assists with the screwing action of the cap 2C in order to seal the chamber 200.

Further FIG. 14 through FIG. 16 are directed to the vibration transferred to the brush unit 5. As mentioned above the coils C generate a magnetic field promoting the reciprocal motion or vibration of the interactive zone 7 which is transferred to the brush 5A by means of the shaft SH. The electric toothbrush assembly housing 2h comprises a resilient material R at the pin bar 6 in order to suppress the vibration transferred to the housing 2h. The housing perimeter increases as one moves towards the opposite end of the portable hygiene kit 1 or away from the brush unit 5 as clearly shown in FIG. 15 and FIG. 16.

FIG. 17 through FIG. 22 is directed to the flossing unit assembly 4. FIG. 17 is a first exemplary embodiment of the flossing unit assembly 4 located at a second distal end of the portable hygiene kit 1. The flossing unit assembly 4 is disengaged or engaged to the second distal end of the portable hygiene kit 1 by attaching means such as screw surface 31. Inside the screw surface a protrusion 41 is located, as shown in FIG. 19, which engages with the receiving hollow shaft 4B located at the flossing unit assembly 4. The flossing unit further comprises a cutter recess 41 with a cutter 42 located at the walls of the flossing unit assembly 4. The cutter serves to cut the amount of the dental floss H needed. The dental floss, as shown in FIG. 20 and FIG. 21, is stored inside the flossing unit assembly 4 around the hollow shaft 4B.

Figure 22:
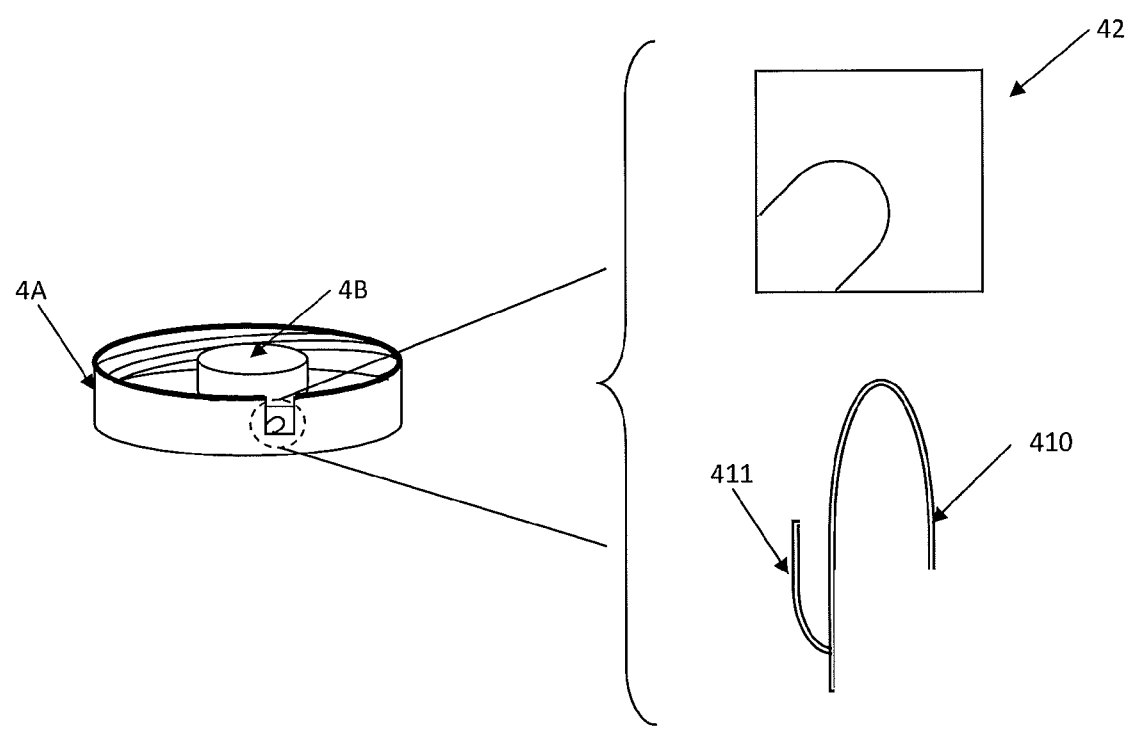
FIG. 22 shows the cutting device attached to the end cap in accordance with the principles of the present invention.
Figure 27:
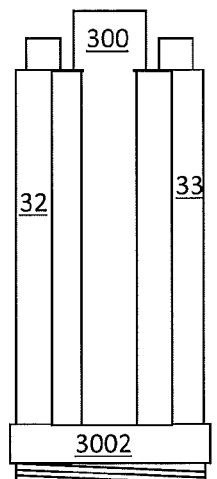
FIG. 26 through FIG. 28 show a first exemplary embodiment of the hygienic material holder of the portable electric toothbrush with hollow shaft in accordance with the principles of the present invention.

The cutter 42, which engages in the cutter recess 41, is made of a material strong enough to provide a physical separation between the dental floss and the portion needed or wanted for flossing. In the instant case, a hard polymer is preferred although other material may be used. The cutter 42 can be integrally made with the flossing unit wall or separated as shown in FIG. 22. The cutter 41 comprises a first curved body 410 that assist with the engagement of the cutter 42 at the cutter recess 41. Further the cutter 42 comprises a second curved body 411 that assist with the cutting procedures of the dental floss H.

FIG. 23 through FIG. 38 are directed to the storage unit 3 and the different exemplary embodiments in accordance with the principles of the present invention. FIG. 23 provides a clear example of the assembling procedures of the portable hygiene kit 1 wherein the electric toothbrush assembly 2 is coupled to the storage unit 3, wherein said storage unit comprises a hygienic material holder 3A having a base 3002, a mouthwash retainer 33, a paste retainer 32, wherein said mouthwash retainer 33 and paste retainer 32 surrounds a holder hollow shaft 300.

FIG. 24 discloses a first exemplary embodiment use of the hygiene material holder 3A wherein the batteries are located inside the holder hollow shaft 300. The present embodiment provides enough area to cover the batteries and terminal extend from said holder hollow shaft 300 in order to provide energy for the actuator.

FIG. 25 discloses a second exemplary embodiment use of the hygiene material holder 3A in accordance with the principles of the present invention. The present embodiment does not provide space for the batteries but further provide space for storing other materials at the holder hollow shaft 300. The batteries are enclosed in chamber 200 as explained above for FIG. 10 trough FIG. 13.

Figure 26:
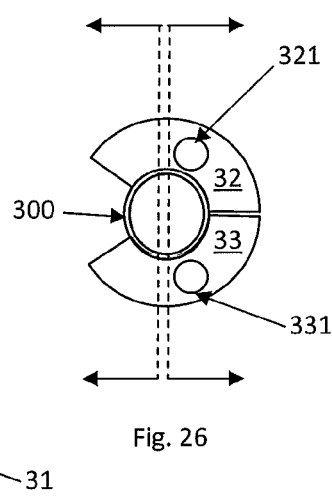
Figure 28:
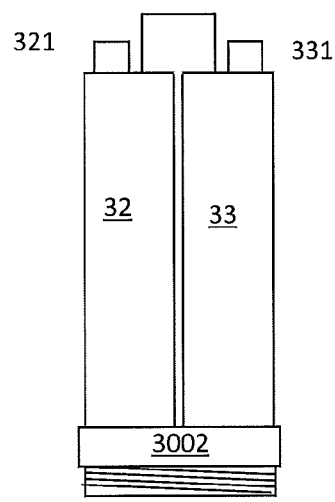
Figure 29:
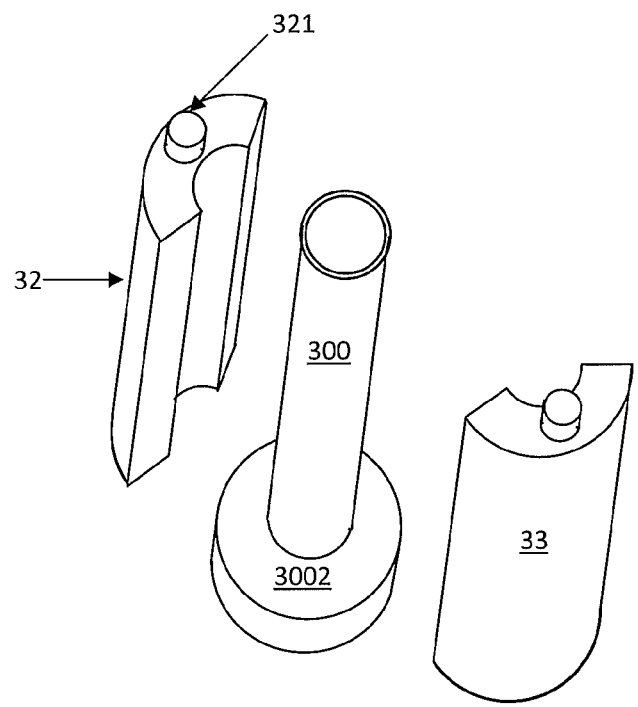
FIG. 29 is an isometric view of the first exemplary embodiment of the hygienic material holder with hollow shaft in accordance with the principles of the present invention.
Figure 30:
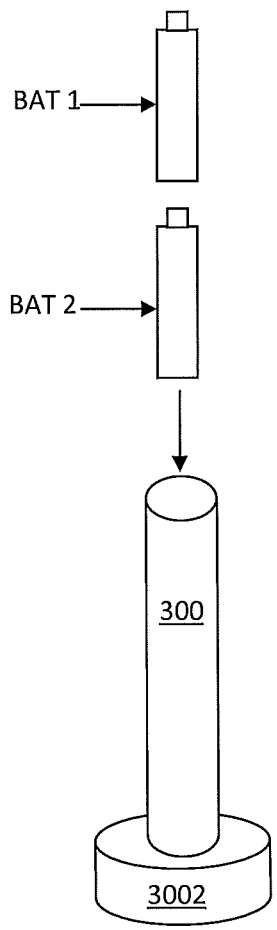
FIG. 30 and FIG. 31 show the hygienic material holder hollow shaft of the portable electric toothbrush in accordance with the principles of the present invention.
Figure 31:
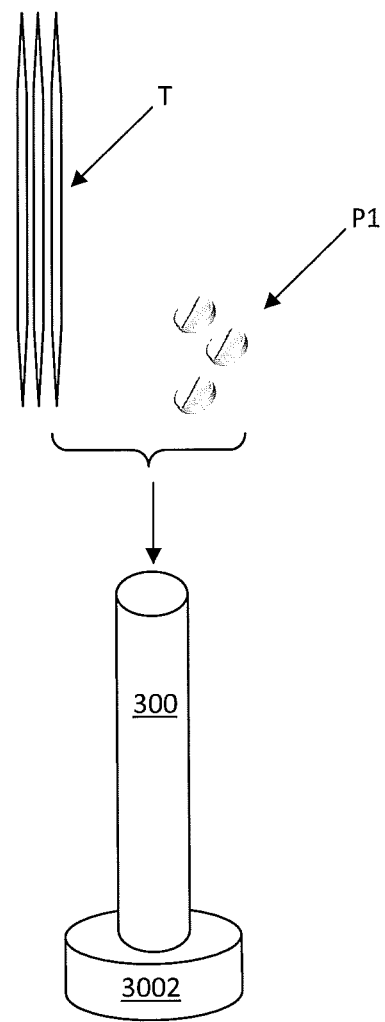

FIG. 26 troughs FIG. 28 are directed to a first exemplary embodiment of the hygiene material holder 3A. As mentioned above, the hygiene material holder 3A comprising a base 3002, a mouthwash retainer 32, a paste retainer 33, wherein said mouthwash retainer 32 and paste retainer 33 surrounds a holder hollow shaft 300. The mouthwash retainer 32 comprises a mouthwash output 321 and said paste retainer 33 comprises a paste output 331. The mouthwash retainer 32 and paste retainer 33 are configured to provide a space while surrounding the holder hollow shaft 300, wherein said space is aligned with the portion of the storage unit forming the recess 5B and brush recess 5C for receiving the retractable brush unit 5. As mentioned the holder hollow shaft 300 may receive batteries, as shown in FIG. 30, or other material such as pills P1 and tooth picks T, as shown in FIG. 31.

Figure 35:
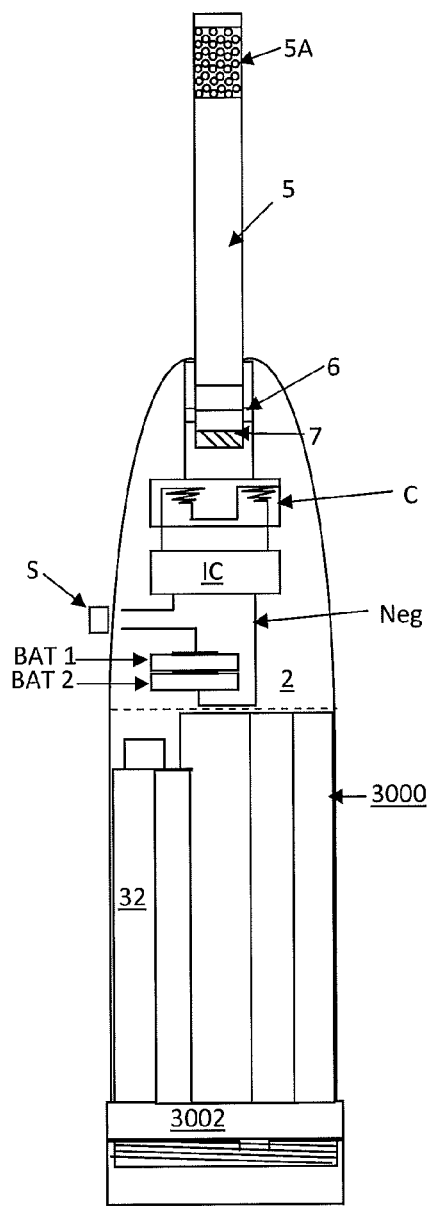
FIG. 35 shows a more detailed assembling of the portable electric toothbrush with the second exemplary embodiment of the hygienic material holder in accordance with the principles of the present invention.
Figure 32:
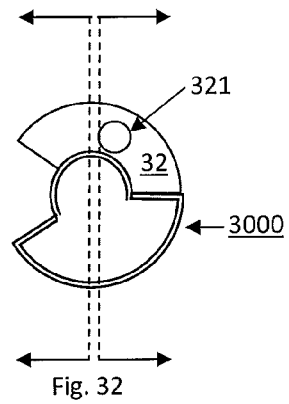
FIG. 32 through FIG. 34 show a second exemplary embodiment of the hygienic material holder of the portable electric toothbrush with hollow shaft in accordance with the principles of the present invention.
Figure 33:
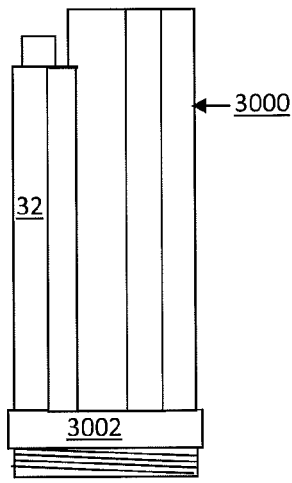
Figure 34:
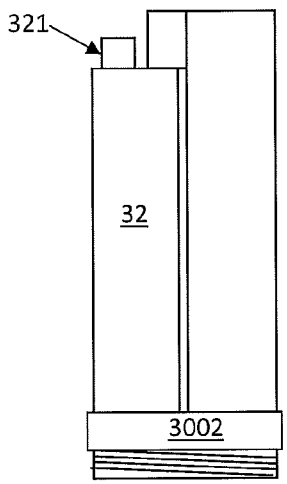

FIG. 32 through FIG. 38 are directed to a second exemplary embodiment of the hygienic material holder 3A. In this case the hygienic material holder 3A comprises a base 3002, a mouthwash retainer 33 and a chamber 3000, as shown in FIG. 32 through FIG. 34. Further, FIG. 35 presents the assembly of said second exemplary embodiment of the hygiene material holder 3A inside the storage unit 3.

Figure 36:
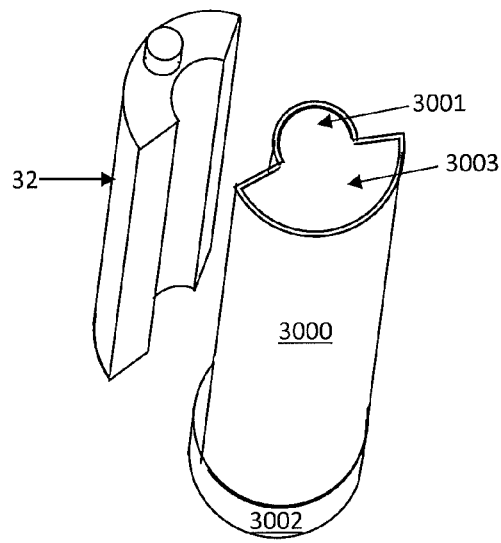
FIG. 36 is an isometric view of the second exemplary embodiment of the hygienic material holder with hollow shaft in accordance with the principles of the present invention.
Figure 37:
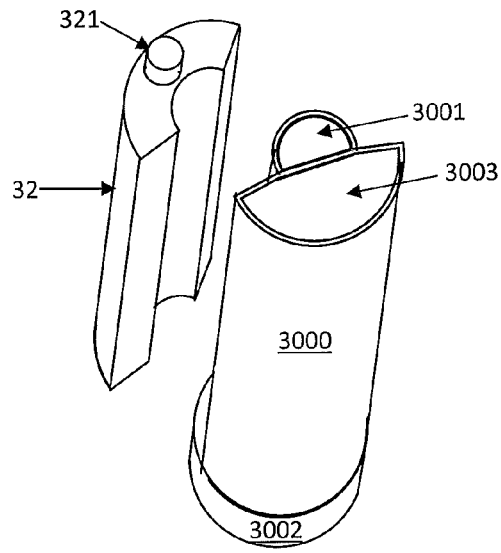
FIG. 37 is an isometric view of a third exemplary embodiment of the hygienic material holder with hollow shaft in accordance with the principles of the present invention.
Figure 38:
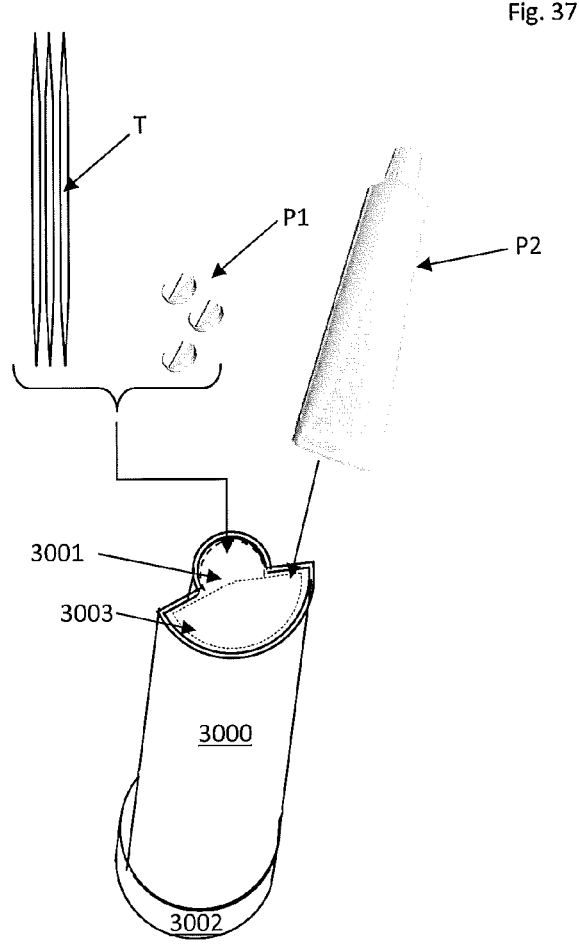
FIG. 38 is an isometric view of the second exemplary embodiment of the hygienic material holder hollow shaft in accordance with the principles of the present invention.

FIG. 36 shows more details of the second exemplary embodiment of the hygienic material holder 3A. The chamber 3000 comprises a second holder hollow shaft 3001 and an open space 3002. FIG. 37 shows a division between the second holder hollow shaft 3001 and the open space 3002 as an alternative, however these two sections can be provided with separation as shown in FIG. 36. Different from the first second exemplary embodiment of the hygienic material holder 3A, the second exemplary embodiment of the hygienic material holder 3A comprises the chamber 3000 to receive a paste tube P2 at the open space 3002. The second holder hollow shaft 3001 further serves to receive other material such as pills P1 and tooth picks T.

The invention is not limited to the precise configuration described above. For example a portable hygiene kit 1 comprising a toothbrush assembly 2 a non-retractable brush unit 5, a storage section 3 and a flossing unit 4, as shown in FIG. 39 can be provided base on the disclosure as explained above. Further, a cover 500 can be provided to avoid contamination. While the invention has been described as having a preferred design, it is understood that many changes, modifications, variations and other uses and applications of the subject invention will, however, become apparent to those skilled in the art without materially departing from the novel teachings and advantages of this invention after considering this specification together with the accompanying drawings. Accordingly, all such changes, modifications, variations and other uses and applications which do not depart from the spirit and scope of the invention are deemed to be covered by this invention as defined in the following claims and their legal equivalents. In the claims, means-plus-function clauses, if any, are intended to cover the structures described herein as performing the recited function and not only structural equivalents but also equivalent structures.

All of the patents, patent applications, and publications recited herein, and in the Declaration attached hereto, if any, are hereby incorporated by reference as if set forth in their entirety herein. All, or substantially all, the components disclosed in such patents may be used in the embodiments of the present invention, as well as equivalents thereof. The details in the patents, patent applications, and publications incorporated by reference herein may be considered to be incorporable at applicant's option, into the claims during prosecution as further limitations in the claims to patently distinguish any amended claims from any applied prior art.

The invention claimed is:

1. A portable hygiene kit comprising:
   a housing comprising a first section, a second section and a third section;
   a electric toothbrush assembly is located at the first section;
   a storage section is located at the second section;
   a flossing unit is located at the third section; and
   a retractable brush unit,
   wherein the storage section comprises a hygiene material holder, said hygiene holder comprising a base, a mouthwash retainer, and a holder hollow shaft,
   wherein the storage section comprises a paste retainer, and
   wherein said mouthwash retainer and said paste retainer surround the holder hollow shaft.

2. The portable hygiene kit as in claim 1,
   wherein said retractable brush unit is attached to the first section housing by mean of a pin bar serving as a pivot for the retractable brush unit.

3. The portable hygiene kit as in claim 1,
   wherein said retractable brush unit comprises:
   a first shaft having a first distal end and a second distal end;
   a brush at a first distal end of the brush unit; and
   an interactive zone at a second distal end.

4. The portable hygiene kit as in claim 3,
   wherein said interactive zone is a zone made of magnetic material.

5. The portable hygiene kit as in claim 3,
   wherein said electric toothbrush assembly comprises an actuator, wherein said actuator generates motion at the interactive zone without physical contact.

6. The portable hygiene kit as in claim 5,
   wherein said actuator comprises at least a battery, an integrated circuit and a bobbin.

7. The portable hygiene kit as in claim 1,
   wherein said housing comprises a first recess, wherein said first recess extends from the first section toward the second section serving as a cover for the retractable brush unit.

8. The portable hygiene kit as in claim 1,
   wherein the flossing unit comprises flossing, a cutter recess, a cutter and hollow shaft.

* * * * *